(12) United States Patent
Wang et al.

(10) Patent No.: US 9,254,085 B2
(45) Date of Patent: Feb. 9, 2016

(54) SYSTEM AND METHOD FOR MONITORING CHANGE OF INTRAOCULAR PRESSURE AND CONTACT LENS FOR SENSING CHANGE OF INTRAOCULAR PRESSURE

(71) Applicant: National Taiwan University, Taipei (TW)

(72) Inventors: Lon Wang, Taipei (TW); Pin-Chung Lin, Taipei (TW); I-Jong Wang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 298 days.

(21) Appl. No.: 13/837,362

(22) Filed: Mar. 15, 2013

(65) Prior Publication Data

US 2014/0163351 A1    Jun. 12, 2014

(30) Foreign Application Priority Data

Dec. 12, 2012  (TW) .............................. 101147040 A

(51) Int. Cl.
*A61B 5/00*   (2006.01)
*A61B 3/16*   (2006.01)
*A61B 3/107*  (2006.01)

(52) U.S. Cl.
CPC .. *A61B 3/16* (2013.01); *A61B 3/107* (2013.01)

(58) Field of Classification Search
CPC .............. A61B 3/10; A61B 3/14; A61B 3/16; A61B 3/107; A61B 3/125; A61B 5/14532
See application file for complete search history.

(56) References Cited

U.S. PATENT DOCUMENTS

| | | | |
|---|---|---|---|
| 6,544,193 B2 * | 4/2003 | Abreu ........................... | 600/558 |
| 6,554,425 B1 * | 4/2003 | Roffman et al. ......... | 351/159.74 |
| 6,749,568 B2 * | 6/2004 | Fleischman et al. .......... | 600/399 |
| 7,137,952 B2 * | 11/2006 | Leonardi et al. .............. | 600/398 |
| 7,594,729 B2 * | 9/2009 | Van Heugten ................ | 351/221 |
| 8,870,371 B2 * | 10/2014 | Ando et al. ............. | 351/159.31 |
| 8,899,753 B2 * | 12/2014 | Steinmueller ................. | 351/221 |
| 8,960,898 B1 * | 2/2015 | Etzkorn et al. ........... | 351/159.03 |
| 8,989,834 B2 * | 3/2015 | Ho et al. ........................ | 600/381 |

* cited by examiner

*Primary Examiner* — Max Hindenburg
(74) *Attorney, Agent, or Firm* — Muncy, Geissler, Olds & Lowe, P.C.

(57) ABSTRACT

A system and a method for monitoring change of intraocular pressure and a contact lens for sensing change of intraocular pressure are provided. The contact lens includes a first material layer and a first pattern. The center of the first material layer has an optical region, and the optical region corresponds to a cornea region of an eyeball. The first pattern is formed on the optical region. Furthermore, the contact lens may further include a second material layer and a second pattern. The second material layer is located on the first material layer. The second pattern is formed on the second material layer and overlaps with the first pattern to form a moire pattern.

18 Claims, 19 Drawing Sheets

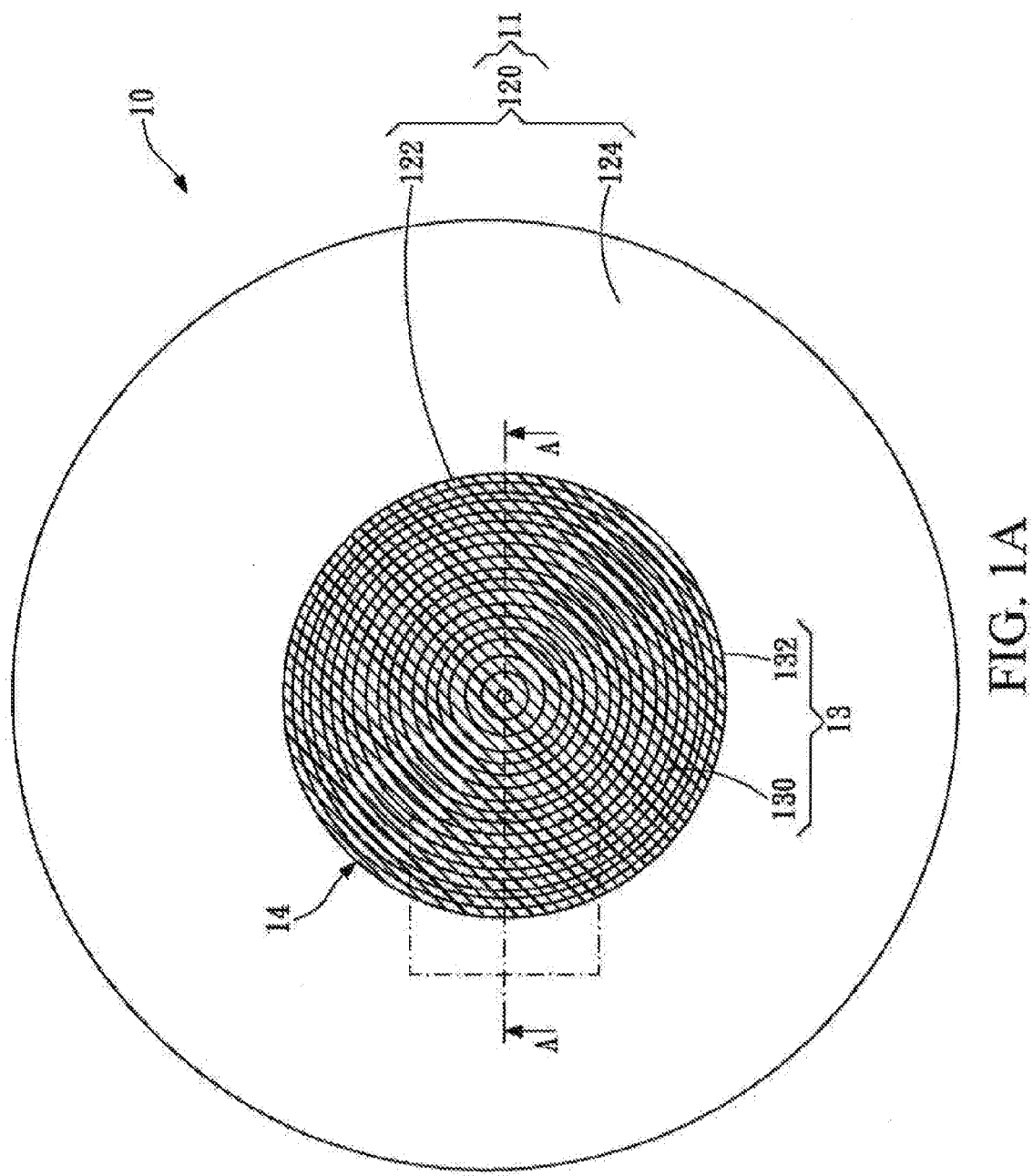

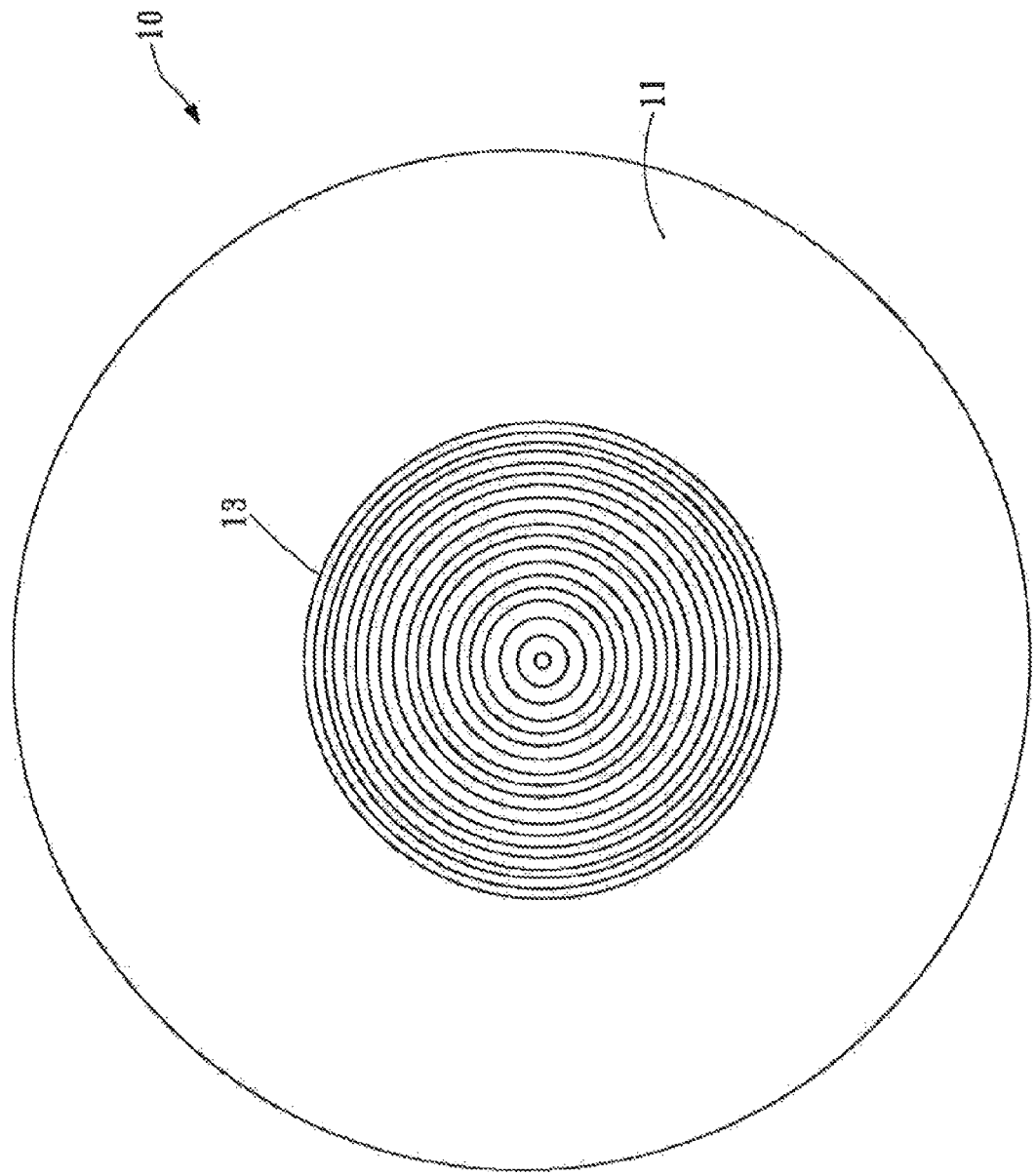

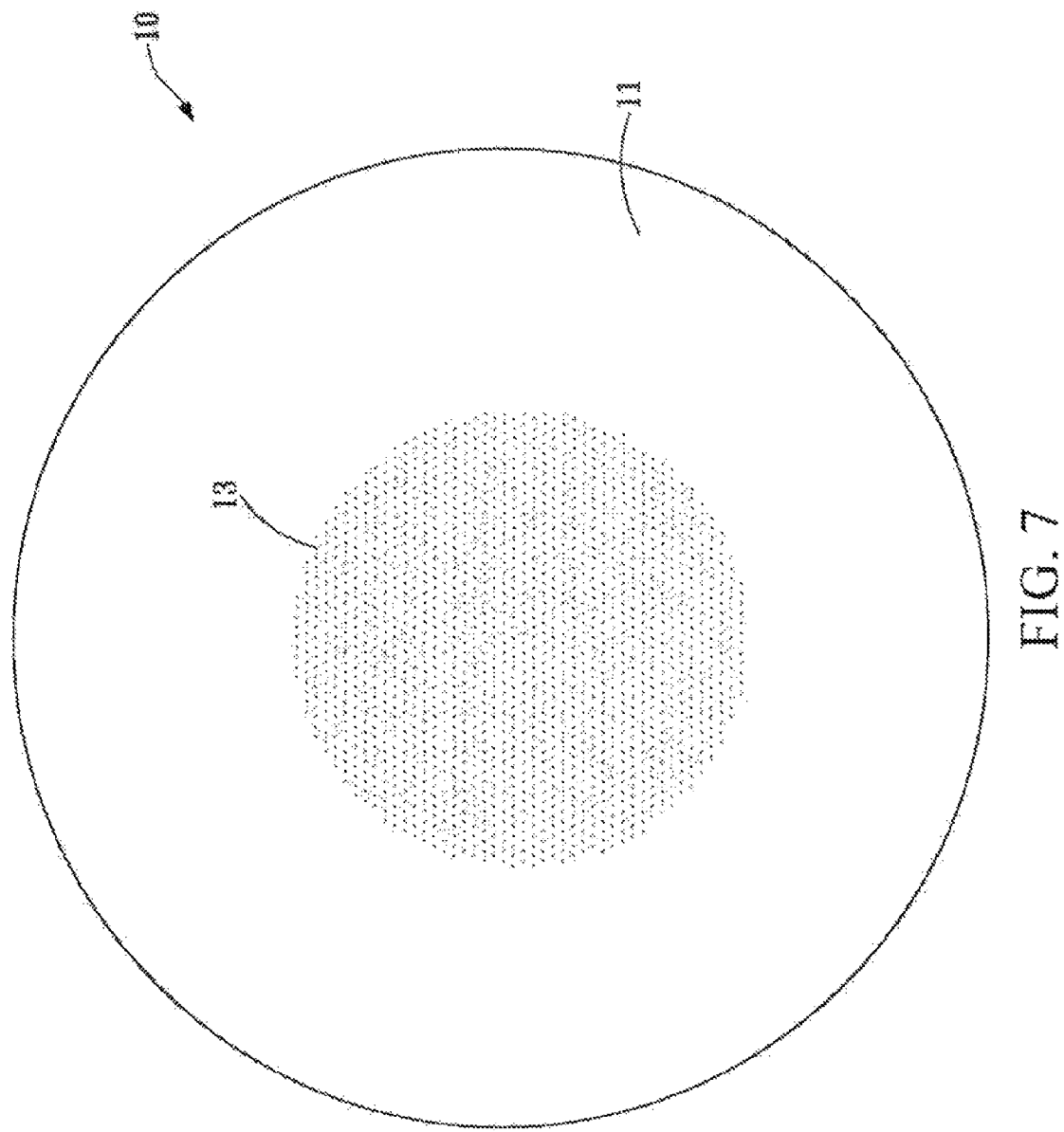

SYSTEM AND METHOD FOR MONITORING CHANGE OF INTRAOCULAR PRESSURE AND CONTACT LENS FOR SENSING CHANGE OF INTRAOCULAR PRESSURE

CROSS-REFERENCES TO RELATED APPLICATIONS

This non-provisional application claims priority under 35 U.S.C. §119(a) on Patent Application No. 101147040 filed in Taiwan. R.O.C. on Dec. 12, 2012, the entire contents of which are hereby incorporated by reference.

BACKGROUND OF THE INVENTION

1. Technical Field

The present invention relates to monitoring technology for an intraocular pressure (IOP), and in particular, to a system and a method for monitoring change of intraocular pressure and a contact lens for sensing an intraocular pressure change.

2. Related Art

An intraocular pressure of a human body is one of the standards for measuring glaucoma. An excessive change in the intraocular pressure causes damage to optic nerves, so if the change in the intraocular pressure can be observed and tracked, the occurrence opportunity of the glaucoma will be reduced.

The most common manner for measuring an intraocular pressure is a contact applanation tonometer, for example, a Goldmann tonometer. However, frequent use of the contact tonometer for measurement causes a burden to eyes of a user, so the contact tonometer cannot be used as a device for long-term monitoring of an intraocular pressure.

The change of the intraocular pressure indirectly causes a cornea curvature change, so the change of the intraocular pressure can be observed through measuring the change in the cornea curvature. For a patient with glaucoma, an excessive change of an instant intraocular pressure value brings about the danger of blindness. Consequently, the monitored change of the intraocular pressure value becomes an important parameter.

Cornea curvature of a human body is generally obtained in the following manner: A projection device is used to project a stripe pattern onto a cornea of the human body, a recorder is used to record an image reflected from a surface of the cornea, and a change amount of the stripe pattern in the reflected image is analyzed to calculate curvature of the cornea surface. During the measurement, the head of the user must be fixed on a bracket of a measuring instrument, so that the eye of the user is located in a measuring region where the measuring instrument can observe the eyeball. After the location of the eyeball is determined, the stripe pattern to be measured is projected to a region where the cornea is located. In this case, the measuring instrument begins to record the change amount of the stripes and converts the recorded data into a height change of the cornea surface, so as to obtain an absolute value of the cornea curvature. However, in this measurement maimer, a professional person is required to assist in operating the instrument, and in the operation process, movement of the user head causes an error in the measurement result. The reflective cornea curvature measurement manner has complex calculation and is limited to the weak reflected image. Therefore, poor contrast of the reflected image increases an error value of the calculated curvature. Additionally, this kind of measuring instrument is usually too large to carry, and therefore is unsuitable to be used as a device for monitoring an intraocular pressure.

SUMMARY

In an embodiment, a contact lens for sensing change of intraocular pressure includes a first material layer and a first pattern.

The center of the first material layer has an optical region, and the optical region corresponds to a cornea area of an eyeball. The first pattern is formed on the optical region. The first pattern is formed of a plurality of sub-patterns arranged at intervals.

In an embodiment, a system for monitoring change of intraocular pressure includes a contact lens for sensing change of intraocular pressure and a detection device.

The contact lens for sensing change of intraocular pressure includes a first material layer, a first pattern, second material layer, and a second pattern. The center of the first material layer has an optical region, and the optical region corresponds to a cornea area of an eyeball. The first pattern is formed on the optical region. The second material layer is located on the first material layer. The second pattern is formed on the second material layer and overlaps with the first pattern to form a moire pattern. The first pattern and the second pattern are formed of a plurality of sub-patterns arranged at intervals.

The detection device includes an image capture unit and a processing unit. The image capture unit is used for sequentially capturing images of the moire pattern according to a time interval; and the processing unit is used for analyzing a period of the moire pattern in each image In an embodiment, a system for monitoring change of intraocular pressure includes a contact lens for sensing change of intraocular pressure and a detection device.

The contact lens for sensing change of intraocular pressure includes a first material layer and a first pattern. The center of the first material layer has an optical region, and the optical region corresponds to a cornea area of an eyeball. The first pattern is formed on the optical region. The first pattern is formed of a plurality of sub-patterns arranged at intervals.

The detection device includes a projection unit, an image capture unit, and a processing unit. The projection unit is used for projecting a second pattern onto the contact lens, so that the second pattern overlaps with the first pattern to form a moire pattern. The image capture unit is used for sequentially capturing images of the moire pattern according to a time interval; and the processing unit is used for analyzing a period of the moire pattern in each image.

In an embodiment, a method for monitoring change of intraocular pressure includes: covering a surface of an eyeball with a contact lens having a first pattern; sequentially capturing, according to a time interval, images of a moire pattern formed by a second pattern and the first pattern that overlap with each other; and analyzing a current period of the moire pattern in each image.

In sum, the system and the method for monitoring change of intraocular pressure and the contact lens for sensing change of intraocular pressure according to the present invention implement long-term monitoring of the change of the intraocular pressure of the user through sensing the cornea curvature. Additionally, the system and the method for monitoring change of intraocular pressure and the contact lens for sensing change of intraocular pressure according to the present invention can accurately measure the cornea without dropping fluorescent agents, thereby avoiding damage or infection of the cornea.

BRIEF DESCRIPTION OF THE DRAWINGS

The present invention will become more fully understood from the detailed description given herein below for illustration only, and thus not limitative of the present invention, wherein:

FIG. 1A is a schematic view of a contact lens for sensing change of intraocular pressure according to a first embodiment of the present invention;

FIG. 6 is a schematic view of a contact lens for sensing change of intraocular pressure according to a sixth embodiment of the present invention;

FIG. 7 is a schematic view of a contact lens for sensing change of intraocular pressure according to a seventh embodiment of the present invention;

DETAILED DESCRIPTION

Figure 1B:
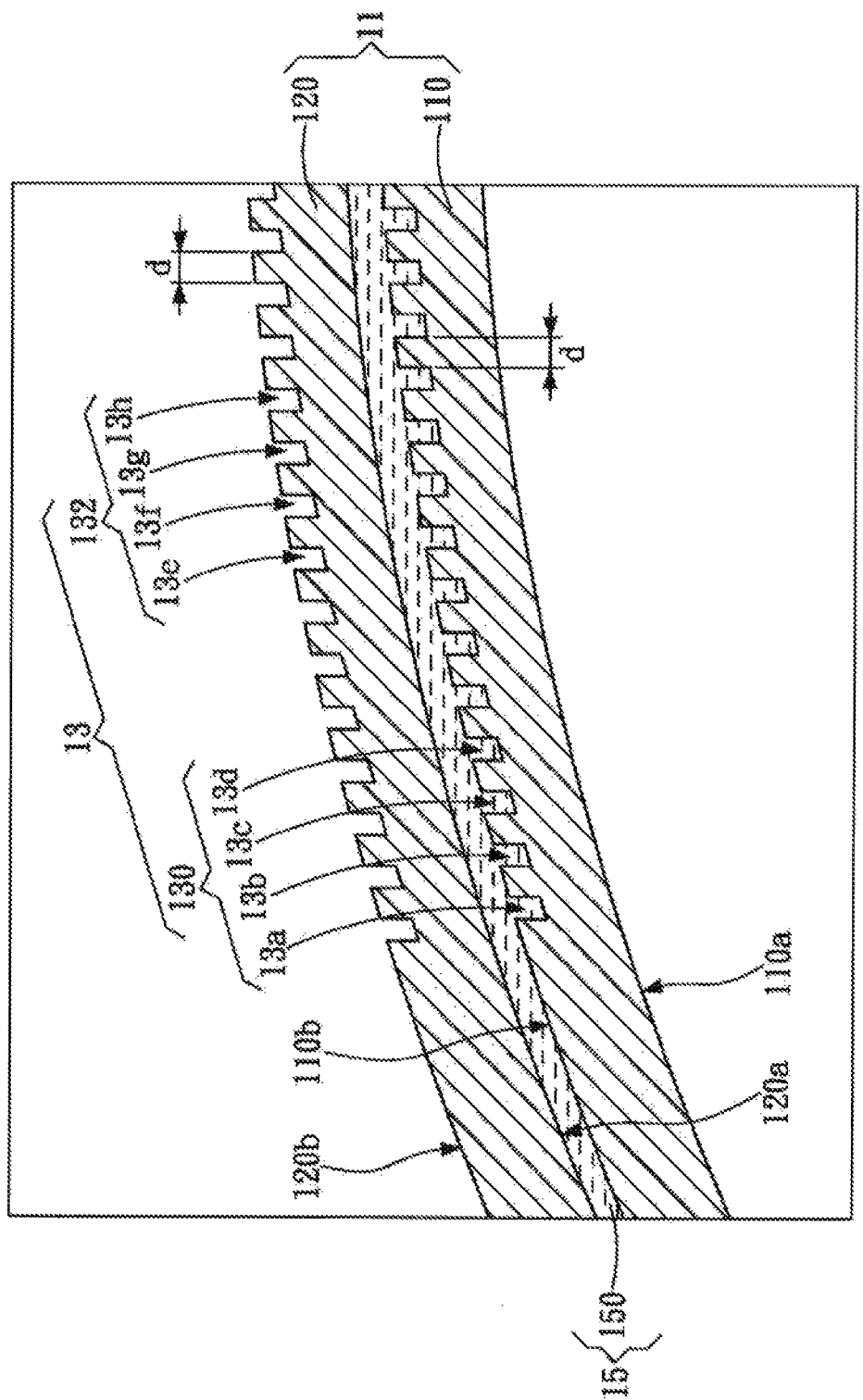
FIG. 1B is a schematic sectional view of a dotted box portion in FIG. 1A based on a cutting line A-A.

Please refer to FIG. 1A, FIG. 1B, FIG. 2A, FIG. 2B, FIG. 3A, FIG. 3B, FIG. 4A, FIG. 4B, FIG. 5A, and FIG. 5B, in which a contact lens 10 for sensing change of intraocular pressure includes a light transmissive material layer 11 (referred to as a first material layer 110 hereinafter), and a pattern 13 (referred to as a first pattern 130 hereinafter).

The first material layer 110 is divided into two regions, that is, an optical region 112 and a non-optical region 114. The optical region 112 is located in the center of the first material layer 110. The non-optical region 114 is located at the periphery of the optical region 112. The optical region 112 corresponds to a cornea region of an eyeball, and a region outside the optical region 112 of the first material layer 110 is the non-optical region 114. In other words, when a user wears the contact lens 10, the optical region 112 covers the cornea region of the eyeball of the user. In some embodiments, the non-optical region 114 surrounds the optical region 112.

The first pattern 130 is formed in the optical region 112 of the first material layer 110. Here, the first material layer 110 has a first surface 110a, and a second surface 110b opposite each other. When the user wears the contact lens 10, the first surface 110a contacts the eyeball of the user. The first pattern 130 is formed in the optical region 112 at the second surface 110b.

Here, the first material layer 110 has curvature, so that when the user wears the contact lens 10, the first material layer 110 is adhered to the eyeball of the user.

Therefore, the curvature of the first material layer 110 is changed as the cornea curvature changes, so that a period T1 of the first pattern 130 is changed accordingly.

In some embodiments, Please refer to FIG. 1A, FIG. 1B, FIG. 2A, FIG. 2B, FIG. 5A, and FIG. 5B, in which the contact lens 10 may further include another light transmissive material layer 11 (referred to as a second material layer 120 hereinafter), and another pattern 13 (referred to as a second pattern 132 hereinafter).

The second material layer 120 is also divided into two regions, that is, an optical region 122 and a non-optical region 124. The optical region 122 is located in the center of the second material layer 120. The non-optical region 124 is located at the periphery of the optical region 122. The optical region 122 corresponds to the cornea region of the eyeball, and a region outside the optical region 122 of the second material layer 120 is the non-optical region 124. In other words, when the user wears the contact lens 10, the optical region 112 covers the cornea region of the eyeball of the user.

The second pattern 132 is formed in the optical region 122 of the second material layer 120. Additionally, the first pattern 130 overlaps with the second pattern 132 to form a moire pattern 14.

Here, the second material layer 120 has a first surface 120a and a second surface 120b opposite each other. The first surface 120a of the second material layer 120 is connected to the second surface 110b of the first material layer 110. In some embodiments, an edge of the first surface 120a of the second material layer 120 is jointed with an edge of the second surface 110b of the first material layer 110.

Figure 2A:
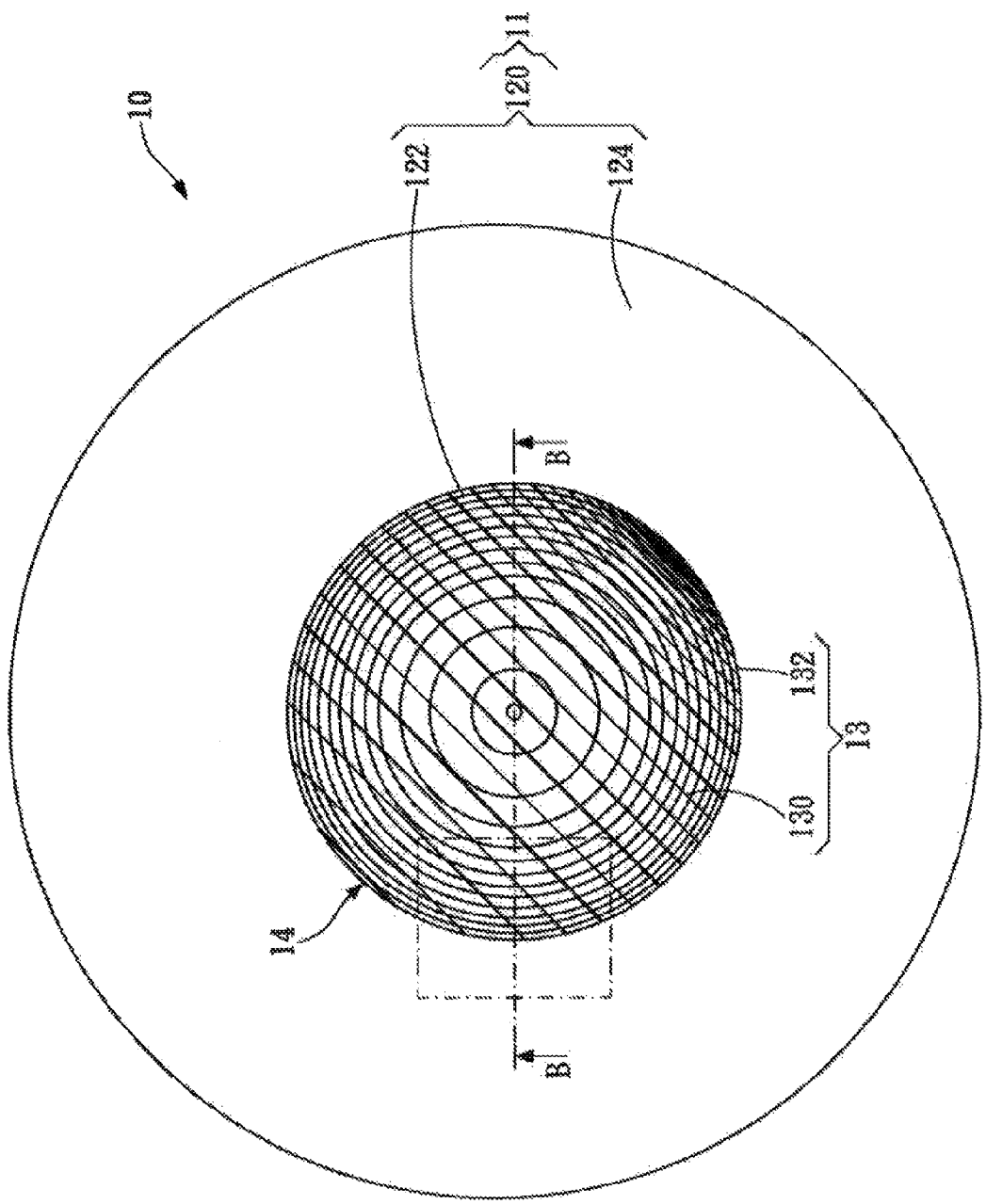
FIG. 2A is a schematic view of a contact lens for sensing change of intraocular pressure according to a second embodiment of the present invention.
Figure 2B:
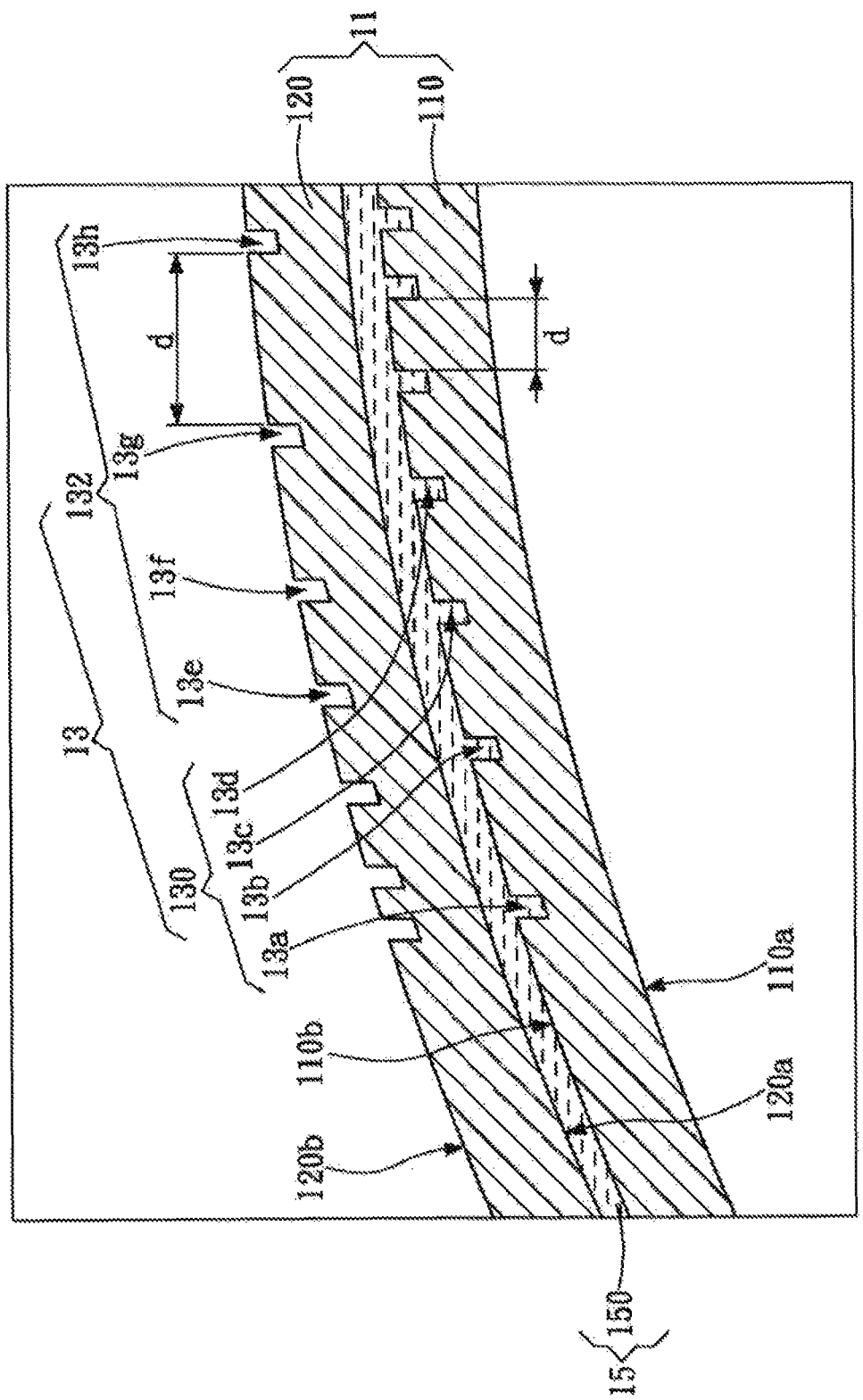
FIG. 2B is a schematic sectional view of a dotted box portion in FIG. 2A based on a cutting line B-B.
Figure 5A:
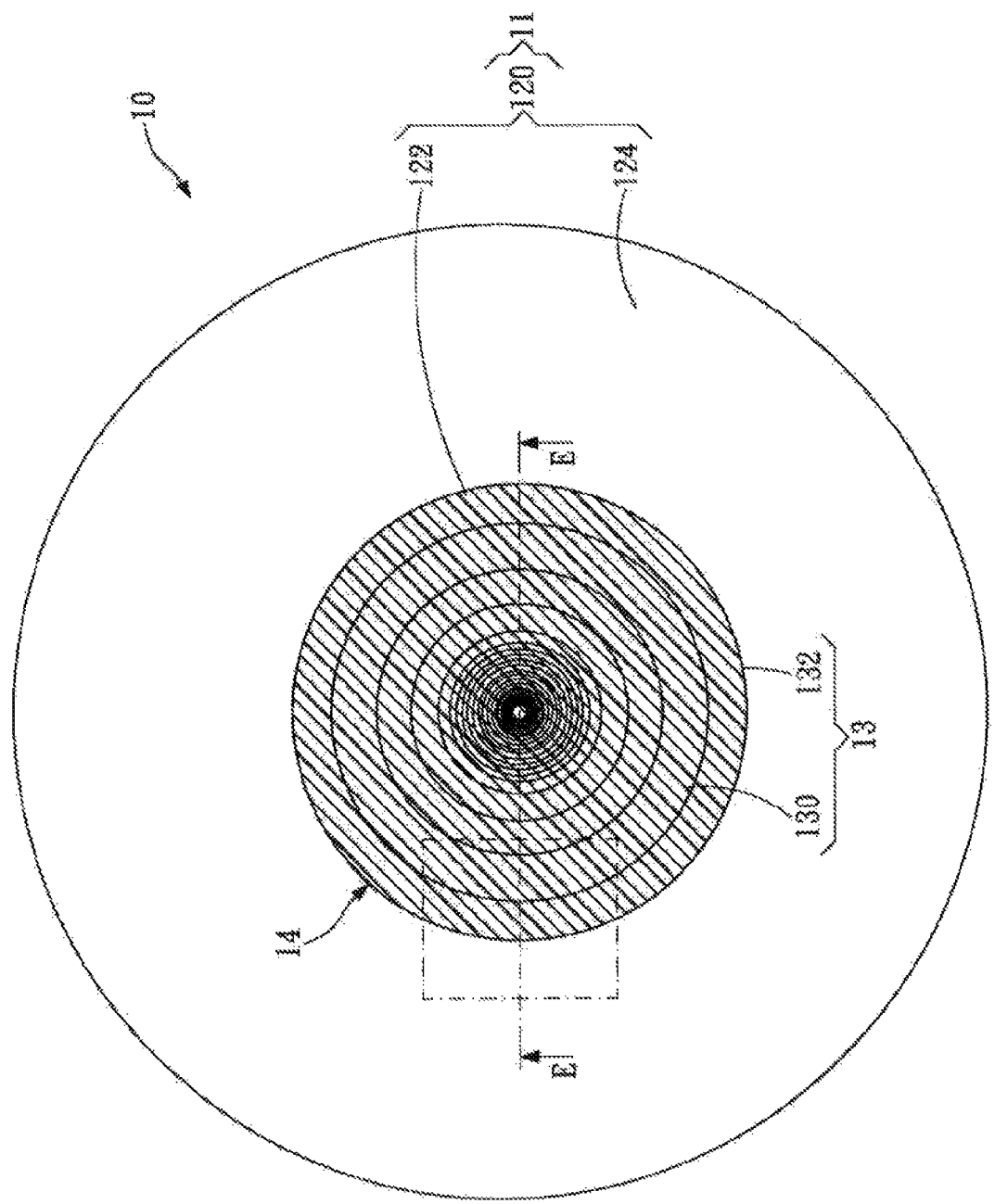
FIG. 5A is a schematic view of a contact lens for sensing change of intraocular pressure according to a fifth embodiment of the present invention.
Figure 5B:
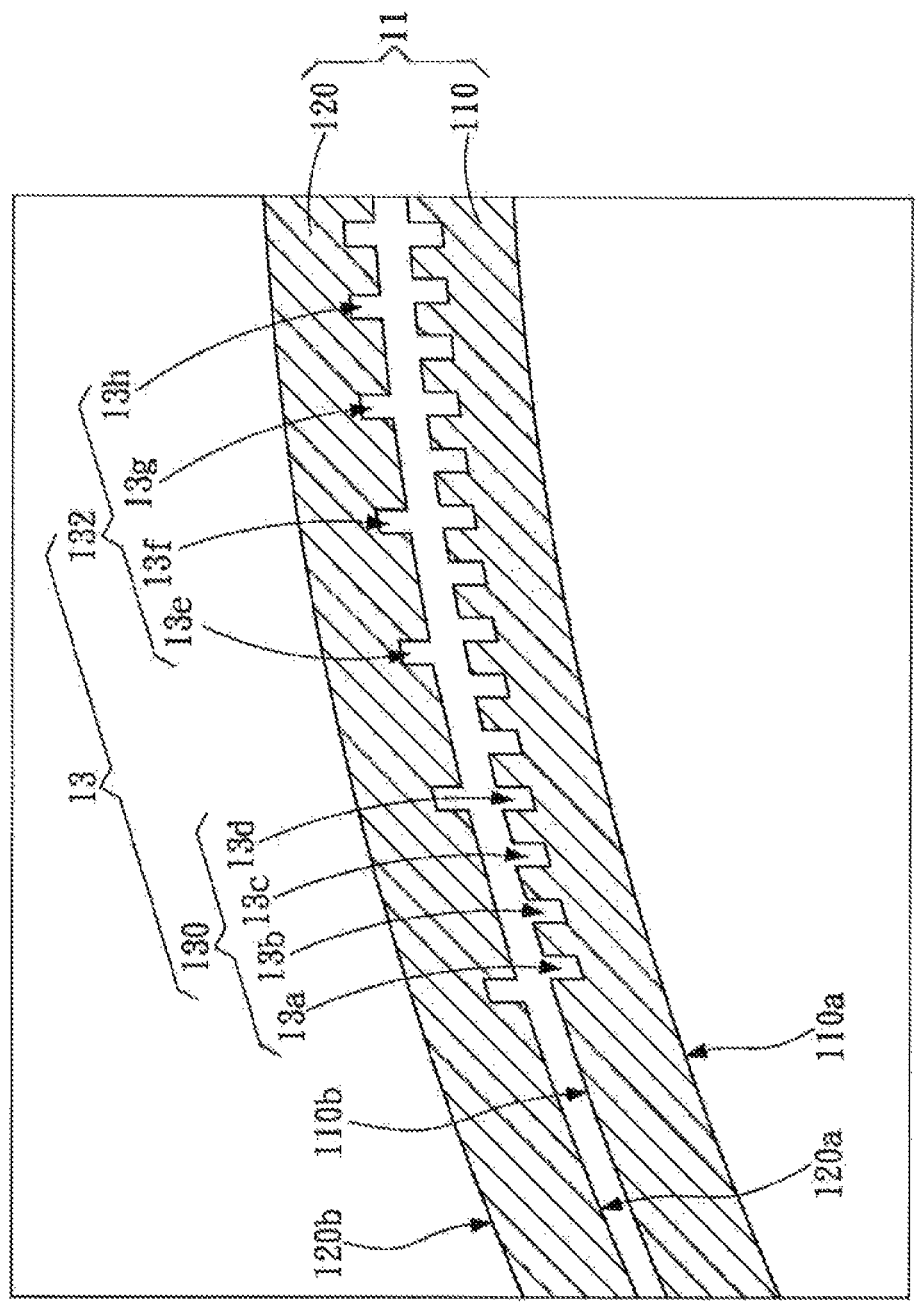
FIG. 5B is a schematic sectional view of a dotted box portion in FIG. 5A based on a cutting line E-E.

In some embodiments, please refer to FIG. 1B, FIG. 2B, and FIG. 5B, in which a buffer layer 15 is sandwiched between the first material layer 110 and the second material layer 120. The buffer layer 15 may be a solution 150 with biocompatibility (as shown in FIG. 1B), such as oil, aquogel, a borate buffer solution, or a phosphate buffer solution, or may be air (as shown in FIG. 2B and FIG. 5B).

The second pattern 132 is formed in the optical region 122 at the first surface 120a of the second material layer 120 (as shown in FIG. 5B), or in the optical region 122 at the second surface 120b (as shown in FIG. 1B and FIG. 2B).

In some embodiments, the first material layer 110 may be a soft contact lens material, and the second material layer 120 may be a rigid contact lens material, so as to improve the sensing sensitivity.

Here, please refer to FIG. 1A, FIG. 1B, FIG. 2A, FIG. 2B, FIG. 3A, FIG. 3B, FIG. 4A, FIG. 4B, FIG. 5A, and FIG. 5B, in which the pattern 13 (that is, the first pattern 130 and the second pattern 132), is formed of a plurality of sub-patterns 13a, 13b, 13c, and 13d/13e, 13f, 13g, and 13h arranged at intervals sequentially.

In some embodiments, in the sub-patterns 13a, 13b, 13c, and 13d or the sub-patterns 13e, 13f, 13g, and 13h, the same distance d may exist between two adjacent sub-patterns, as shown in FIG. 1A, FIG. 1B, FIG. 3A, and FIG. 3B. In other words, the pattern 13 may be a periodic pattern. When the pattern 13 is a periodic pattern, the plurality of sub-patterns 13a, 13b, 13c, and 13d/13e, 13f, 13g, and 13h is arranged with equal distances d sequentially.

In some embodiments, in the sub-patterns 13a, 13b, 13c, and 13d or the sub-patterns 13e, 13f, 13g, and 13h, the distance d between two adjacent sub-patterns varies, as shown in FIG. 2A, FIG. 2B, FIG. 4A, and FIG. 4B. In other words, the pattern 13 may be a non-periodic pattern. When the pattern 13 is a non-periodic pattern, the plurality of sub-patterns 13a, 13b, 13c, and 13d/13e, 13f, 13g, and 13h is arranged with different distances d sequentially. For example, for the first pattern 130, the plurality of sub-patterns 13a, 13b, 13c, and 13d may be arranged sequentially with ascending distances d from right to left, with descending distances d from right to left, with ascending distances d from inside to outside, or with descending distances d from inside to outside, or in other manners with randomly changing distances. For the second pattern 132, the plurality of sub-patterns 13e, 13f, 13g, and 13h may be arranged sequentially with ascending distances d from right to left, with descending distances d from right to left, with ascending distances d from inside to outside, or with descending distances d from inside to outside, or in other manners with randomly changing distances.

In some embodiments, the two patterns 13 in the contact lens 10 are both periodic patterns, as shown in FIG. 1A and FIG. 1B.

In some embodiments, the two patterns 13 in the contact lens 10 are both non-periodic patterns, as shown in FIG. 2A and FIG. 2B.

In some embodiments, one of the two patterns 13 in the contact lens 10 is a periodic pattern, and the other one is a non-periodic pattern. For example, in FIG. 5A and FIG. 5B, the first pattern 130 is a periodic pattern and the second pattern 132 is a non-periodic pattern.

Figure 3A:
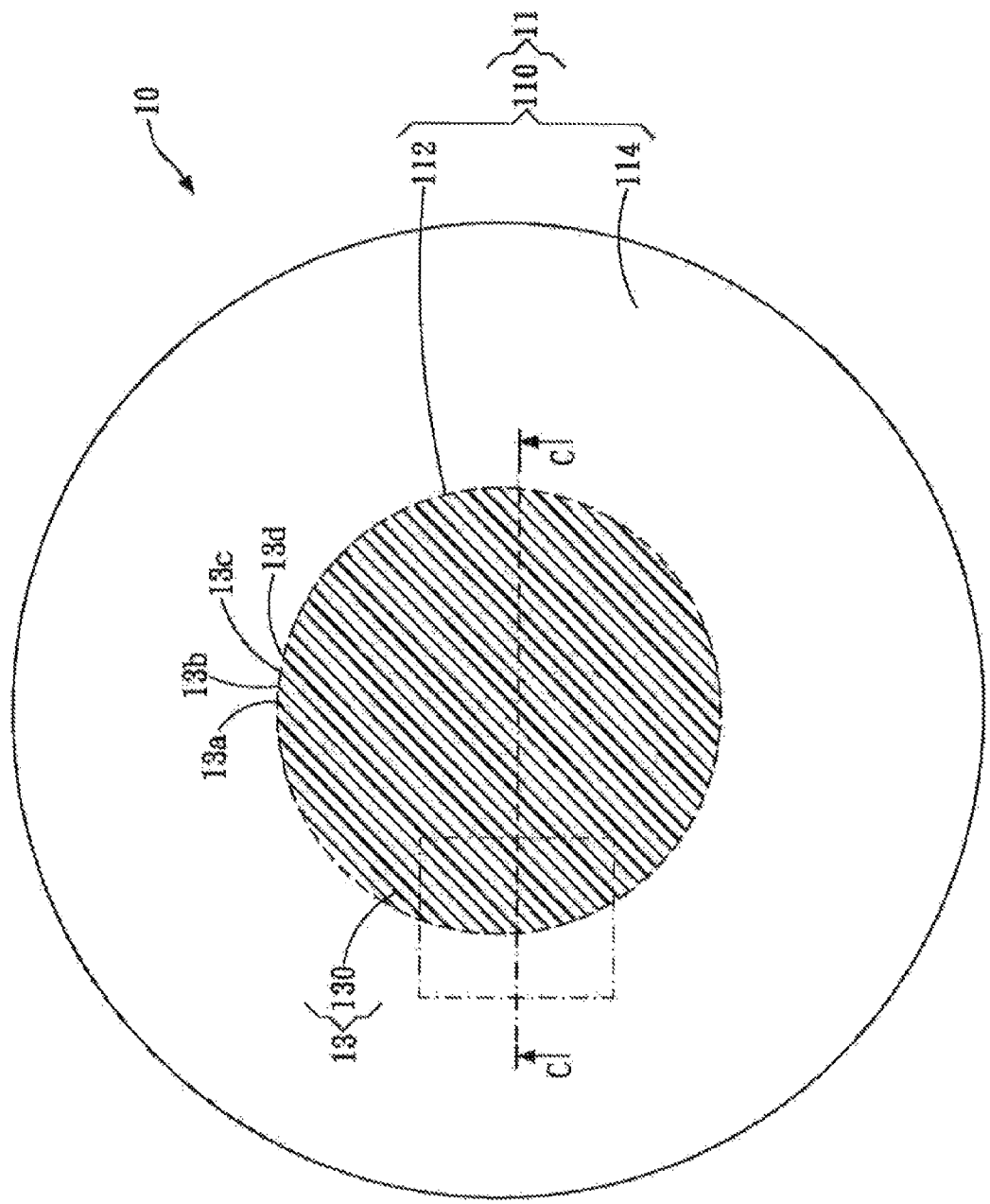
FIG. 3A is a schematic view of a contact lens for sensing change of intraocular pressure according to a third embodiment of the present invention.
Figure 3B:
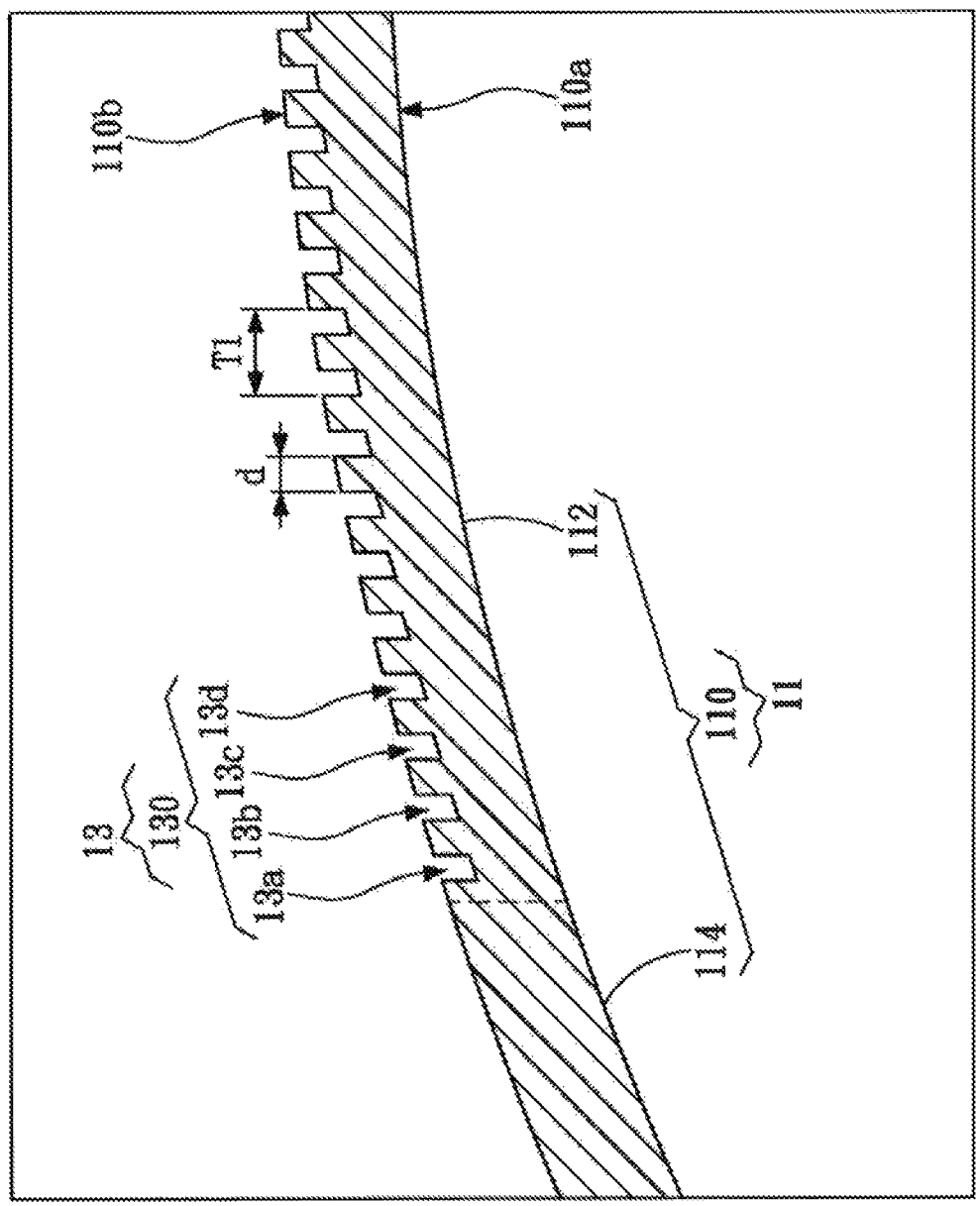
FIG. 3B is a schematic sectional view of a dotted box portion in FIG. 3A based on a cutting line C-C.
Figure 4A:
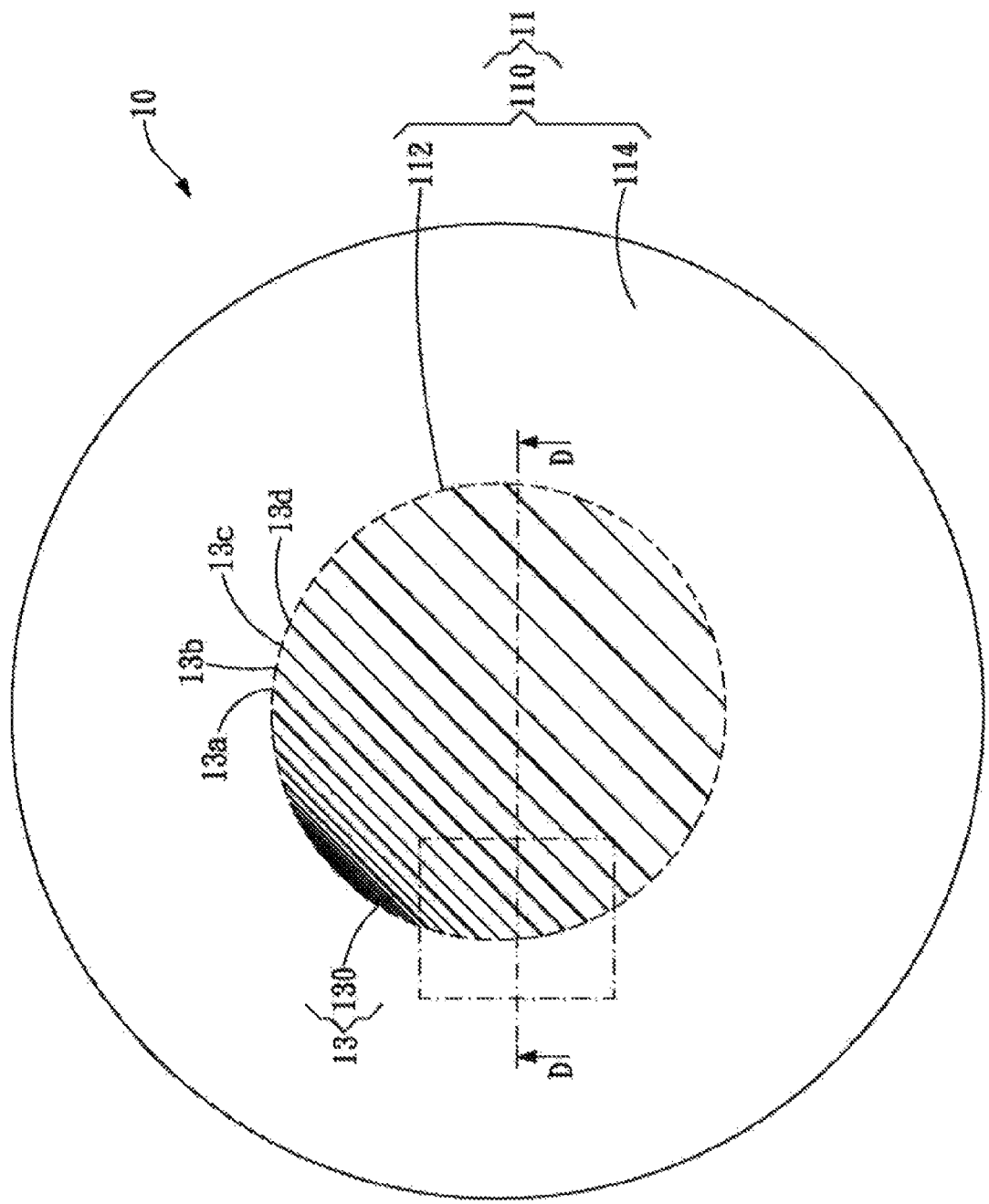
FIG. 4A is a schematic view of a contact lens for sensing change of intraocular pressure according to a fourth embodiment of the present invention.
Figure 4B:
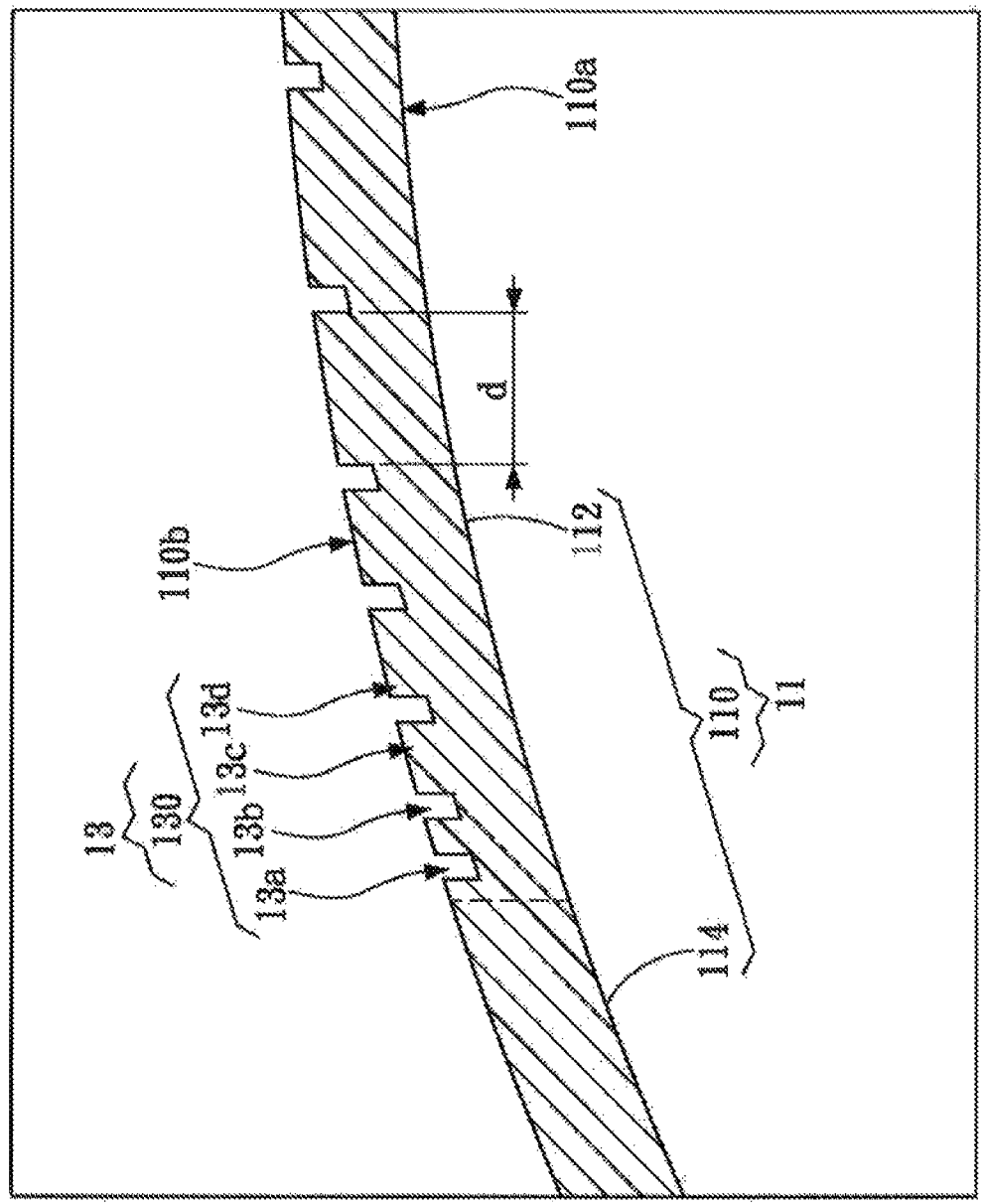
FIG. 4B is a schematic sectional view of a dotted box portion in FIG. 4A based on a cutting line D-D.

Each sub-pattern 13a/13b/13c/13d/13e/13f/13g/13h may be a line of any shape (as shown in FIG. 3A and FIG. 4A), a ring (as shown in FIG. 6), a point of any shape (as shown in FIG. 7), and the like. The any shape is, for example, a circle, a triangle, a rectangle, or any other polygon. The line is taken as an example; please refer to FIG. 3A and FIG. 4A, in which the pattern 13 may be a plurality of lines arranged at intervals, so as to form a stripe pattern. The ring is taken as an example; please refer to FIG. 6, in which the pattern 13 may be formed of a plurality of rings with different inner diameters, where the rings have the same circle center. The circular point is taken as an example; please refer to FIG. 7, in which the pattern 13 may be a plurality of circular points arranged in an array.

In some embodiments, the first pattern 130 and the second pattern 132 are different patterns. For example, in FIG. 1A, FIG. 2A, and FIG. 5A, the first pattern 130 is a plurality of lines and the second pattern 132 is a plurality of rings.

Figure 8:
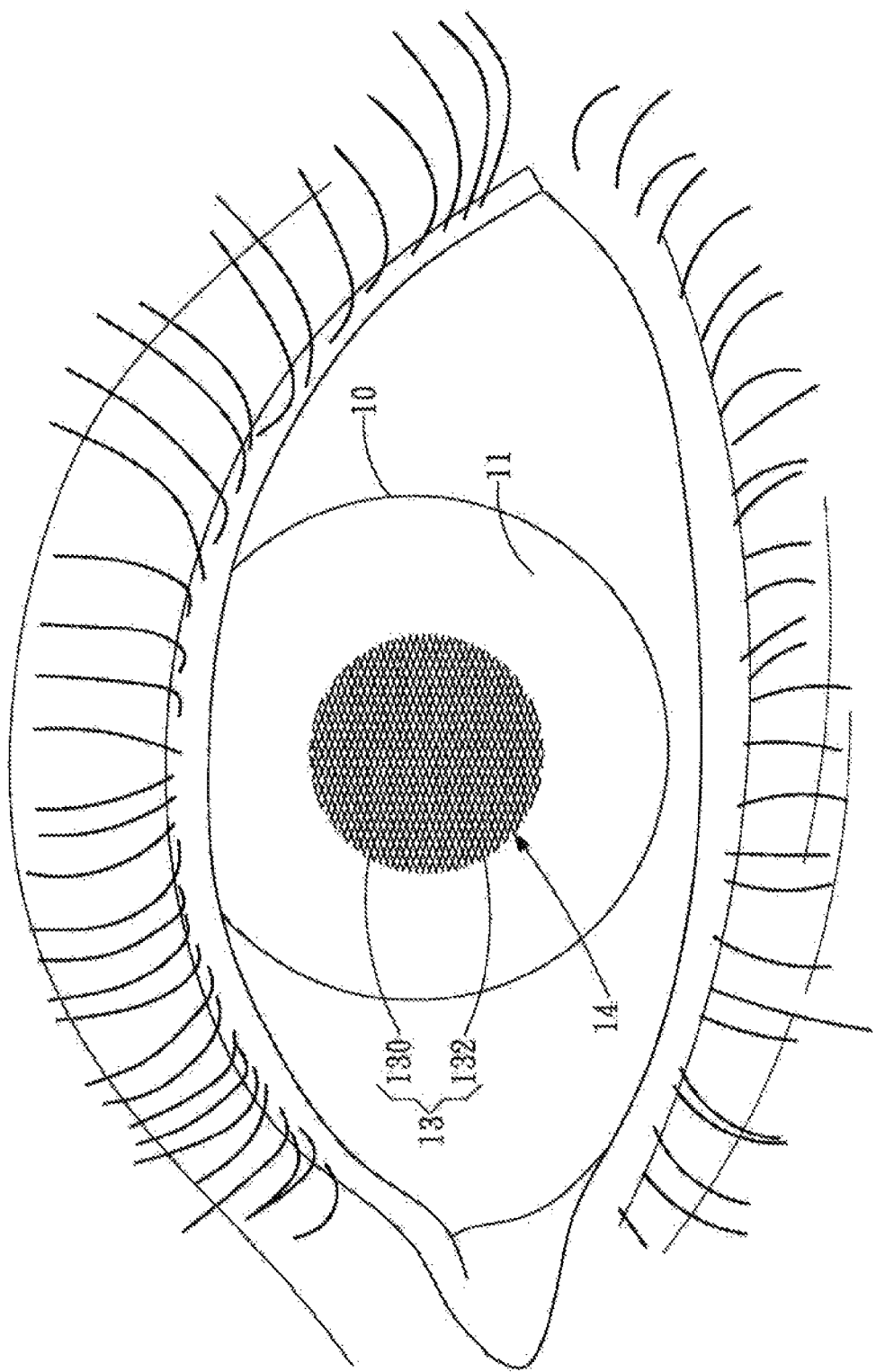
FIG. 8 is a view illustrating a use state of a contact lens for sensing change of intraocular pressure according to an eighth embodiment of the present invention.

In some embodiments, the first pattern 130 and the second pattern 132 are the same pattern. For example, in FIG. 8, both the first pattern 130 and the second pattern 132 are a plurality of lines.

In some embodiments, please refer to FIG. 1B, FIG. 2B, FIG. 3B, FIG. 4B, and FIG. 5B, in which each sub-pattern 13a/13b/13c/13d/13e/13f/13g/13h of the pattern 13 (that is, the first pattern 130 or the second pattern 132) may be a groove on the light transmissive material layer 11 (that is, the first material layer 110 or the second material layer 120). In other words, the pattern 13 is a plurality of grooves provided on the surface of the light transmissive material layer 11 and arranged at intervals. For example, the sub-patterns 13a, 13b, 13c, and 13d of the first pattern 130 are a plurality of grooves arranged at intervals on the second surface 110b of the first material layer 110. The sub-patterns 13e, 13f, 13g, and 13h of the second pattern 132 are a plurality of grooves arranged at intervals on the first surface 120a or the second surface 120b of the second material layer 120. In other words, the sub-pattern is implemented through the groove, so a specific pattern is presented macroscopically.

In some embodiments, bumps corresponding to the grooves may be preformed through a photolithography process on an inner surface of a mould for forming the contact lens 10, so that the pattern 13 and the light transmissive material layer 11 are integrally formed.

In some embodiments, a pigment or dye may also be applied to or printed on the plurality of sub-patterns 13a, 13b, 13c, and 13d/13e, 13f, 13g, and 13h of the pattern 13 arranged at intervals and formed on the surface (for example, the second surface 110b, the first surface 120a or the second surface 120b) of the light transmissive material layer 11. The types and the applying method or printing method of pigments or dye are well known in the prior art, which are not described again.

In some embodiments, the sensitivity of sensing the change of the intraocular pressure (that is, an eyeball curvature change) may be determined by the distance d between two adjacent sub-patterns 13a and 13b/13b and 13c/13c and 13d/13e and 13f/13f and 13g/13g and 13h. In other words, the smaller the distance d between the two adjacent sub-patterns 13a and 13b/13b and 13c/13c and 13d/13e and 13f/13f and 13g/13g and 13h is, the higher the sensitivity is.

In some embodiments, the distance d between the two adjacent sub-patterns 13a and 13b/13b and 13c/13c and 13d/13e and 13f/13f and 13g/13g and 13h may be approximately more than 40 μm. In some embodiments, the distance d between the two adjacent sub-patterns 13a and 13b/13b and 13c/13c and 13d/13e and 13f/13f and 13g/13g and 13h may be preferably about 50 μm.

Figure 9:
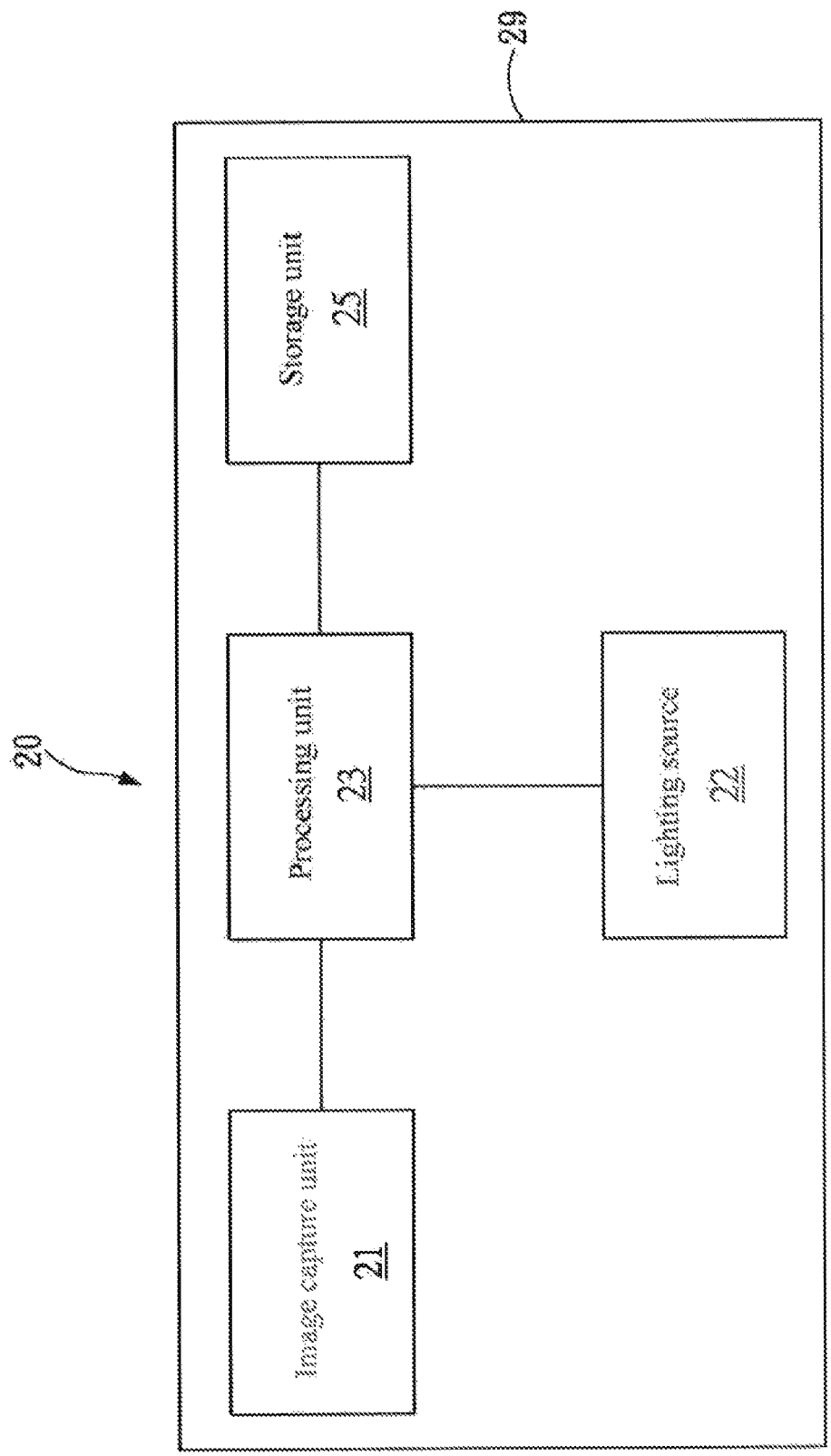
FIG. 9 is a schematic block diagram of a detection device according to an embodiment of the present invention.
Figure 10:
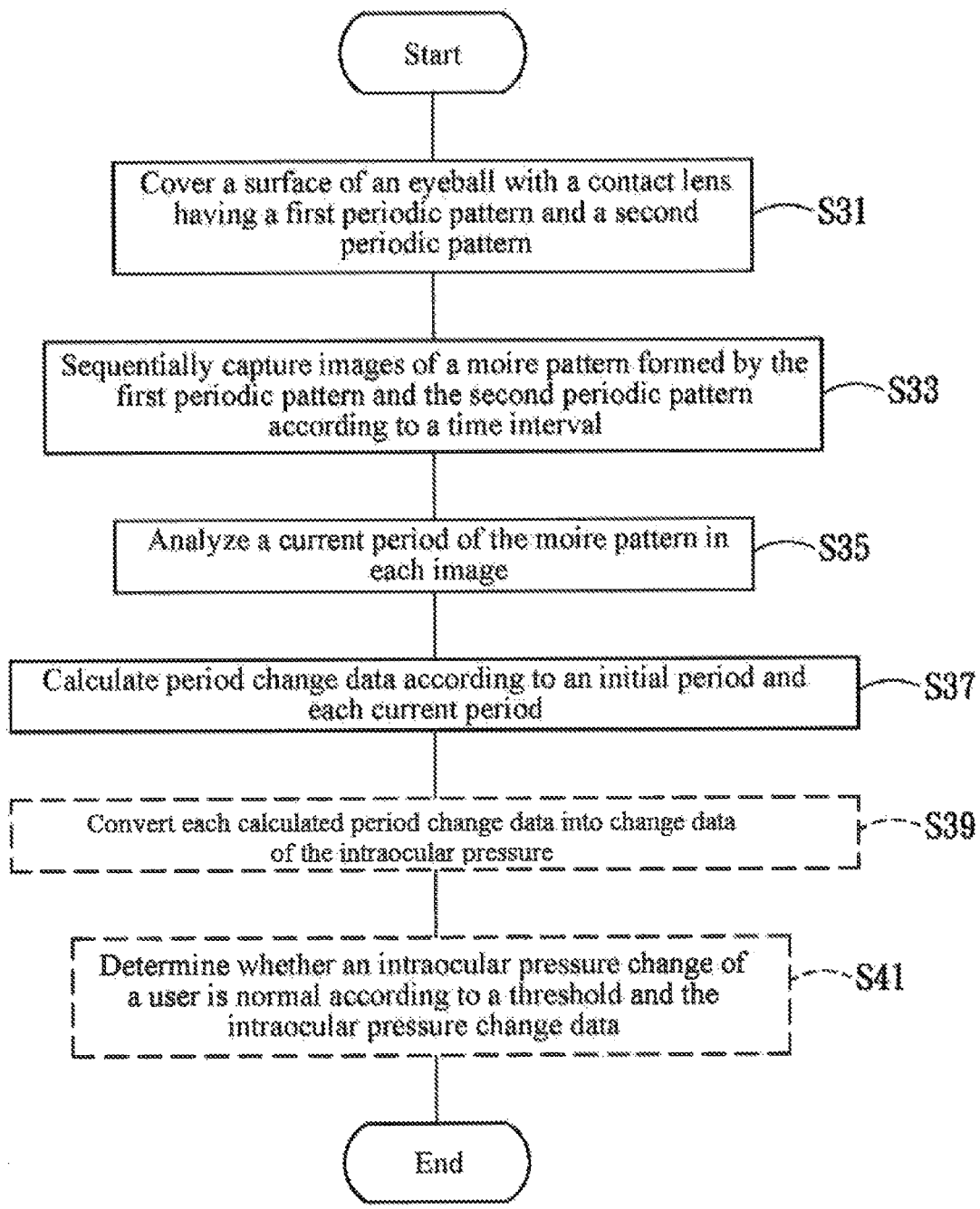
FIG. 10 is a flow chart of a method for monitoring change of intraocular pressure according to an embodiment of the present invention.
Figure 11:
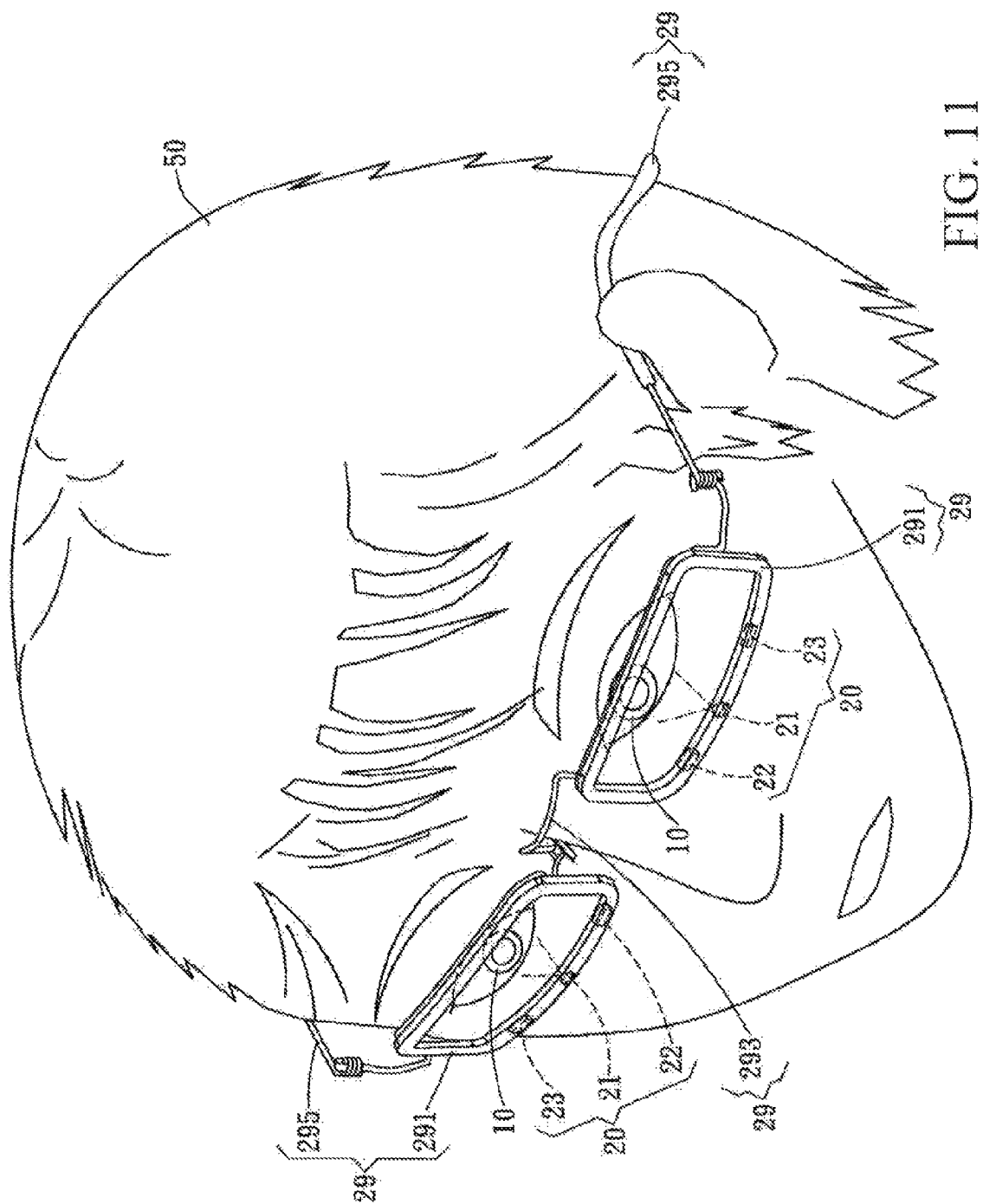
FIG. 11 is a view illustrating a use state of a system for monitoring change of intraocular pressure according to an embodiment of the present invention.

Here, please refer to FIG. 9, FIG. 10, and FIG. 11, in which the contact lens 10 for sensing change of intraocular pressure may be used in combination with a detection device 20, so as to provide long-term and real-time intraocular pressure monitoring.

To monitor a used intraocular pressure, first, a contact lens 10 with a first pattern 130 and a second pattern 132 is covered on a surface of an eyeball of a user (Step S31).

The detection device 20 includes an image capture unit 21 and a processing unit 23.

The image capture unit 21 is electrically connected to the processing unit 23. The image capture unit 21 sequentially captures images of a moire pattern 14 formed by the first pattern 130 and the second pattern 132 according to a time interval, to sequentially obtain a plurality of moire images (Step S33).

In other words, during the monitoring process, the image capture unit 21 regularly captures the image of the moire pattern 14, so as to obtain a moire image of the moire pattern 14 at each monitoring time point during the monitoring process in real time.

The processing unit 23 analyzes a current period of the moire pattern in each moire image (Step S35), and calculates period change data according to an initial period and each current period of the moire pattern (Step S37).

In some embodiments, the moire pattern 14 is operated in a solution, for example, water, tears, and the like.

In some embodiments, the detection device 20 may further include a storage unit 25. The storage unit 25 is electrically connected to the processing unit 23.

The storage unit 25 stores data information about the correspondence between the period change data and change data of the intraocular pressure. In this case, the processing unit 23 may further convert each calculated period change data into the change data of the intraocular pressure according to the stored data information (Step S39).

In some embodiments, the storage unit 25 further stores a threshold. In this case, the processing unit 23 can determine whether the change of the intraocular pressure of a user is normal according to the threshold and the change data of the intraocular pressure (Step S41).

In some embodiments, the initial period of the moire pattern 14 may be pre-stored in the storage unit 25, or is a current period of a moire pattern 14 obtained at the first time (that is, a first monitoring time point) when the user wears the contact lens.

Figure 12:
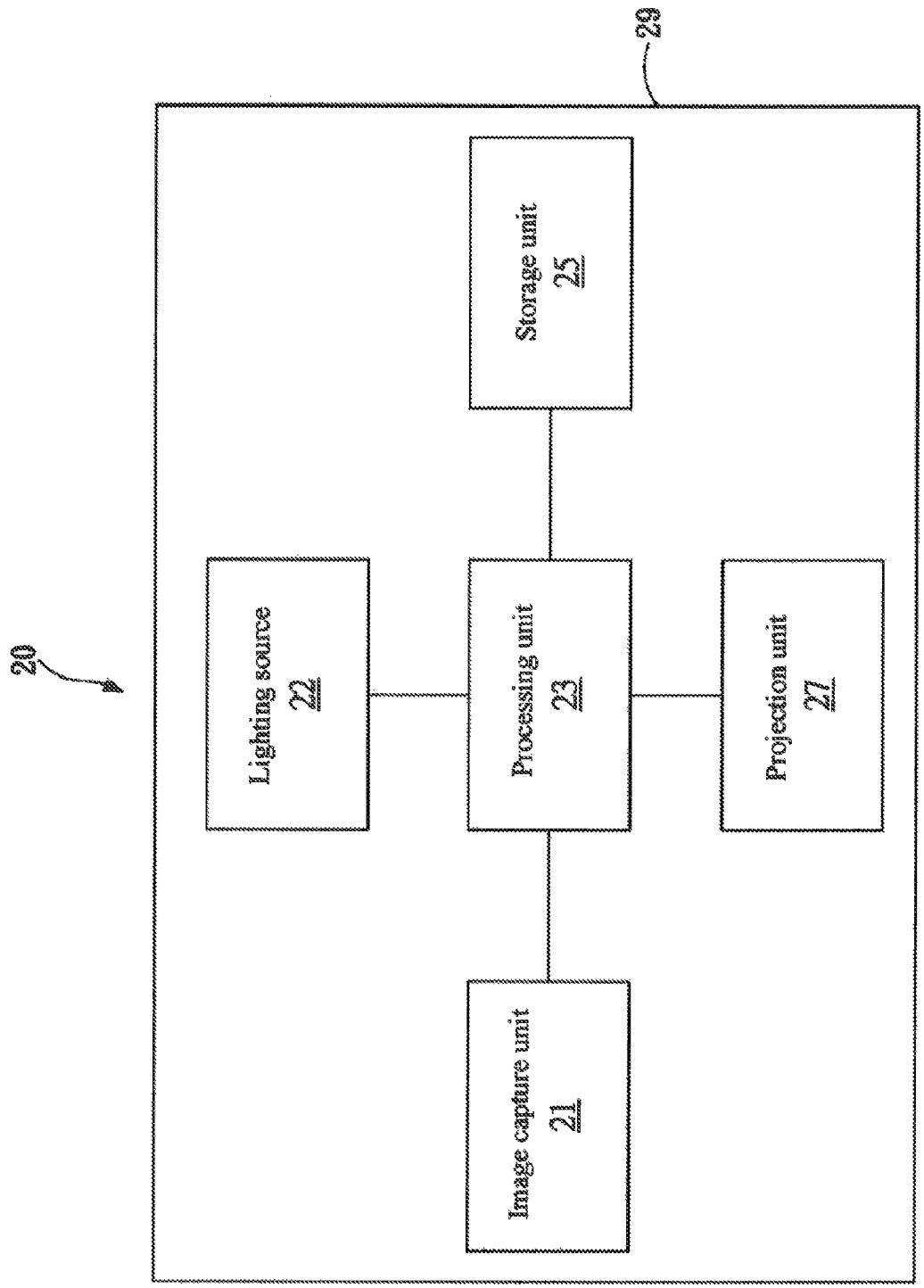
FIG. 12 is a schematic block diagram of a detection device according to another embodiment of the present invention.
Figure 13:
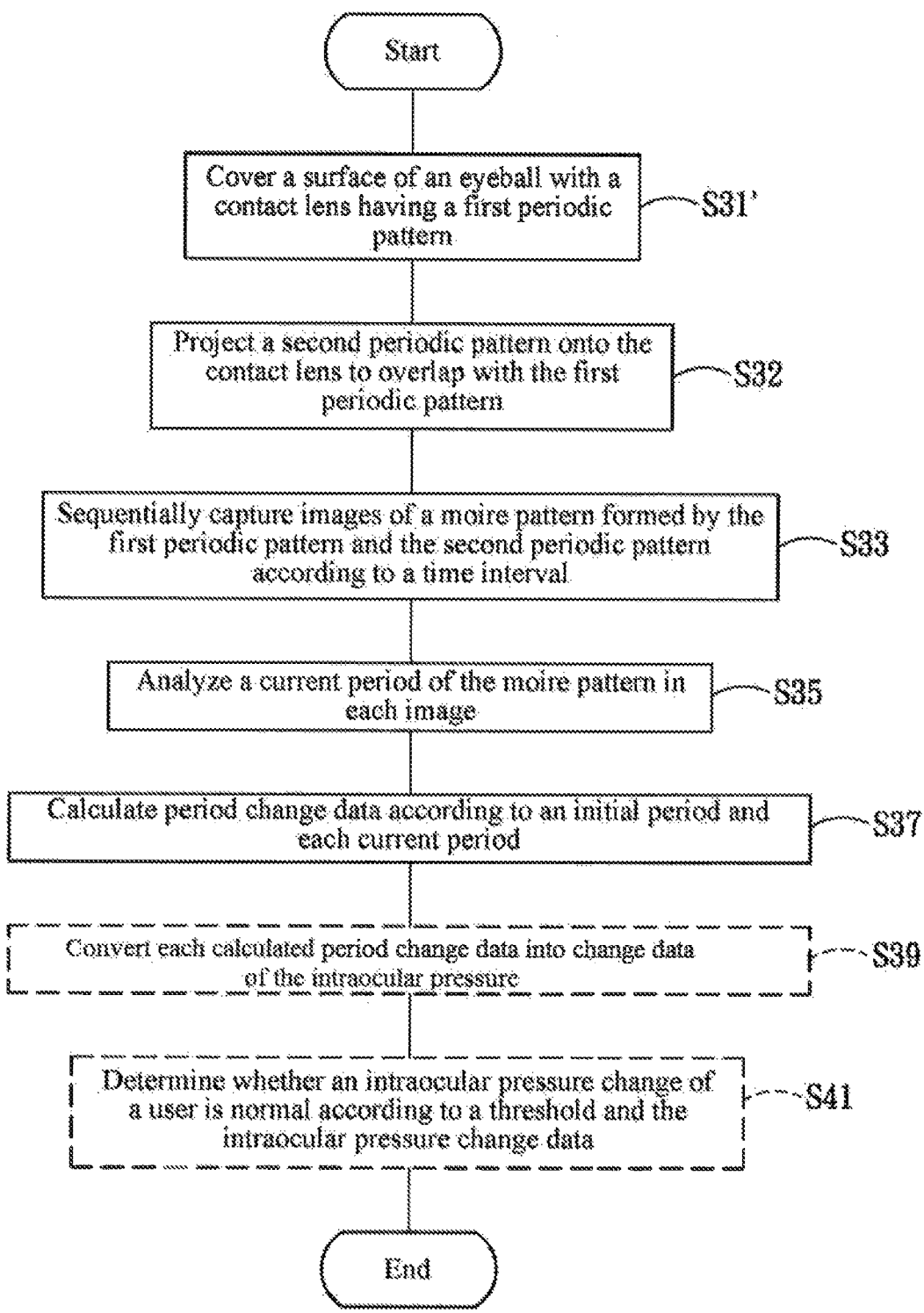
FIG. 13 is a flow chart of a method for monitoring change of intraocular pressure according to another embodiment of the present invention.
Figure 14:
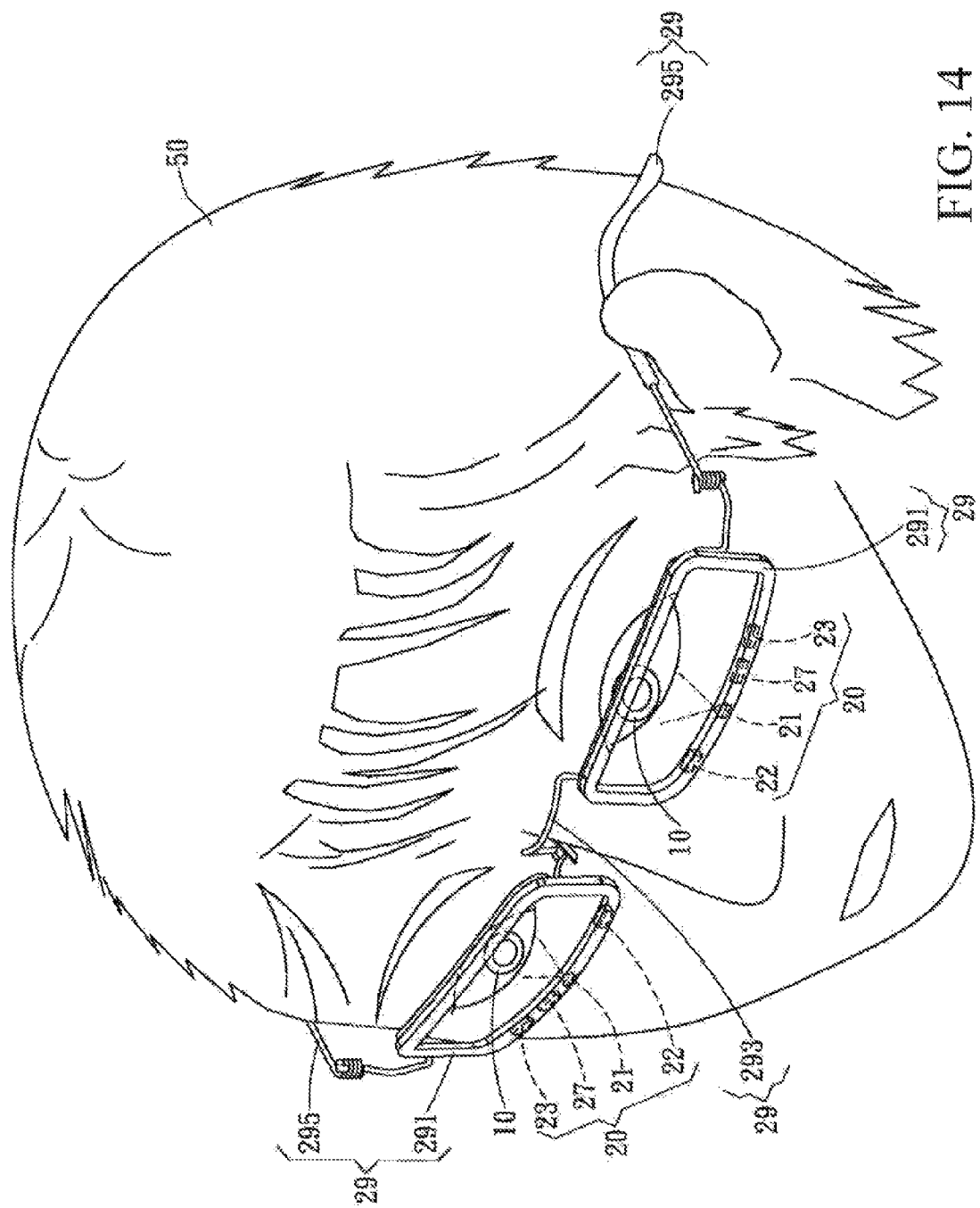
FIG. 14 is a view illustrating a use state of a system for monitoring change of intraocular pressure according to another embodiment of the present invention.

In some embodiments, please refer to FIG. 12, FIG. 13, and FIG. 14, in which the detection device 20 may further include a projection unit 27. The projection unit 27 is electrically connected to the processing unit 23, so as to control running of the projection unit 27 through the processing unit 23.

In this case, the second pattern 132 is projected onto the contact lens 10 by the projection unit 27, and overlaps with the first pattern 130 in the contact lens 10 to form a moire pattern 14 (Step S32). In other words, the contact lens 10 covering the surface of the eyeball of the user does not need to be provided with the second pattern 132 (step S31'). Here, a graph of the second pattern 132 projected by the projection unit 27 is applicable to the graph design of the foregoing second pattern 132, which is not described again.

In some embodiments, under the control of the processing unit 23, the projection unit 27 may project the second pattern 132 only when the image capture unit 21 captures an image. In other words, after the image capture unit 21 completes image capturing, the projection unit 27 may stop projecting the second pattern 132 under the control of the processing unit 23, so as to reduce images with common definition viewed by the user.

In some embodiments, please refer to FIG. 9, FIG. 11, FIG. 12, and FIG. 14, in which the detection device 20 may further include a lighting source 22. The lighting source 22 is electrically connected to the processing unit 23. The lighting source 22 can provide enough brightness for the moire pattern 14, facilitating image capturing of the image capture unit 21.

In some embodiments, please refer to FIG. 11 and FIG. 14, in which the detection device 20 may further include a carrier 29. The carrier 29 may be formed as common glasses. To perform monitoring, a user 50 may wear common glasses (that is, the carrier 29), and the contact lens 10 for sensing the change of the intraocular pressure at the same time, so as to achieve long-term monitoring of the change of the intraocular pressure of the user 50 at any time and any place.

In this case, the processing unit 23 and the storage unit may be disposed inside the carrier 29. The image capture unit 21 is embedded at an inner side of the carrier 29.

For example, the carrier 29 is common glasses, and common glasses include two lens frames 291, a connection frame 293, and two hanger frames 295. First sides of outer edges of the two lens frames 291 are connected to two ends of the connection frame 293 respectively, and each of second sides of the outer edges of the two lens frames 291 is connected to one end of each of the two hanger frames 295. Additionally, when the user 50 wears common glasses, the other end of each hanger frame 295 extends towards the user 50. The first side of the outer edge of each lens frame 291 is opposite the second side of the outer edge. Here, an inner edge of each lens frame 291 refers to an edge for mounting a lens, and the outer edge is opposite the inner edge.

The image capture unit 23 is embedded at an inner side of the lens frame 291, that is, a side where the lens frame 29 extends towards the hanger frame 295. Additionally, when the user 50 wears common glasses, a capture lens of the image capture unit 23 faces a cornea region of an eyeball of the user 50.

When the detection device 20 has a projection device 27, the projection device 27 is disposed on the carrier 29 in a manner approximately same as the disposing manner of the image capture unit 23, so that the projection device 27 can project the second pattern 132 onto the first pattern 130 in the optical region 112 of the contact lens 10.

When the detection device 20 has a lighting source 22, the lighting source 22 is disposed on the carrier 29 in a manner approximately same as the disposing manner of the image capture unit 23, so that the lighting source 22 can provide light rays required by the image capture unit 23 to capture an image.

In sum, the system and the method for monitoring change of intraocular pressure and the contact lens for sensing change of intraocular pressure according to the present invention implements long-term monitoring of the change of the intraocular pressure of the user through sensing the cornea curvature. Additionally, the system and the method for monitoring change of intraocular pressure and the contact lens for sensing change of intraocular pressure according to the present invention can accurately measure the cornea without dropping fluorescent agents and can avoid the damage or infection of the cornea. In some embodiments, in the system and the method for monitoring change of intraocular pressure and the contact lens for sensing change of intraocular pressure according to the present invention, the structure of the pattern and the main body (namely, the light transmissive material), of the contact lens are integrally formed and do not contact the eyeball, thereby not affecting the wearing comfort. In some embodiments, the architecture of the whole detection device is common glasses, so that the user can monitor the intraocular pressure at any time and any place.

While the present invention has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A contact lens for sensing change of intraocular pressure, comprising:

a first material layer, wherein the center of the first material layer has an optical region, and the optical region corresponds to a cornea area of an eyeball; and a first pattern, formed on the optical region, the first pattern being formed of a plurality of sub-patterns arranged at intervals;

a second material layer, being on the first material layer; and a second pattern, being on the second material layer and overlapping with the first pattern to form a moire pattern, wherein the second pattern is formed of a plurality of sub-patterns arranged at intervals.

2. The contact lens for sensing change of intraocular pressure according to claim 1, wherein the first material layer is a soft contact lens material.

3. The contact lens for sensing change of intraocular pressure according to claim 1, wherein the first material layer has a first surface for contacting an eyeball and a second surface opposite the first surface, and the sub-patterns are a plurality of grooves arranged at intervals on the second surface.

4. The contact lens for sensing change of intraocular pressure according to claim 1, wherein the second material layer is a rigid contact lens material.

5. The contact lens for sensing change of intraocular pressure according to claim 1, wherein the sub-patterns of the second pattern are a plurality of grooves arranged at intervals on a surface of the second material layer.

6. A system for monitoring change of intraocular pressure, comprising:
a contact lens comprising:
a first material layer, wherein the center of the first material layer has an optical region, and the optical region corresponds to a cornea area of an eyeball; and
a first pattern, formed on the optical region, the first pattern being formed of a plurality of sub-patterns arranged at intervals;
a second material layer, being on the first material layer; and
a second pattern, being on the second material layer and overlapping with the first pattern to form a moire pattern, wherein the second pattern is formed of a plurality of sub-patterns arranged at intervals; and
a detection device comprising:
an image capture unit, used for sequentially capturing images of the moire pattern according to a time interval; and
a processing unit, used for analyzing a period of the moire pattern in each image to evaluate intraocular pressure according to the period.

7. The system for monitoring change of intraocular pressure according to claim 6, wherein the detection device further comprises:
a carrier, used for a user to wear,
wherein the image capture unit and the processing unit are disposed on the carrier.

8. The system for monitoring change of intraocular pressure according to claim 6, wherein the second material layer is a rigid contact lens material.

9. The system for monitoring change of intraocular pressure according to claim 6, wherein the sub-patterns of the second pattern are a plurality of grooves arranged at intervals on a surface of the second material layer.

10. A method for monitoring change of intraocular pressure, comprising:
covering a surface of an eyeball with a contact lens having a first pattern, the first pattern being formed of a plurality of sub-patterns arranged at intervals;
sequentially capturing, according to a time interval, images of a moire pattern formed by a second pattern and the first pattern that overlap with each other, the second pattern being formed of a plurality of sub-patterns arranged at intervals; and
analyzing a current period of the moire pattern in each image to evaluate intraocular pressure according to the current period.

11. The method for monitoring change of intraocular pressure according to claim 10, wherein the first pattern is formed on a soft contact lens material of the contact lens.

12. The method for monitoring change of intraocular pressure according to claim 10, wherein the first pattern is a plurality of grooves arranged at intervals on a surface of the contact lens.

13. The method for monitoring change of intraocular pressure according to claim 10, further comprising:
projecting the second pattern on the contact lens.

14. The method for monitoring change of intraocular pressure according to claim 13, further comprising:
calculating period change data according to an initial period and each current period.

15. The method for monitoring change of intraocular pressure according to claim 10, wherein the first pattern and the second pattern are formed on two surfaces of the contact lens respectively.

16. The method for monitoring change of intraocular pressure according to claim 15, wherein the first pattern is formed on the soft contact lens material of the contact lens, and the second pattern is formed on a rigid contact lens material of the contact lens.

17. The method for monitoring change of intraocular pressure according to claim 15, wherein the sub-patterns of the first pattern and the sub-patterns of the second pattern are a plurality of grooves arranged at intervals on the two surfaces of the contact lens respectively.

18. The method for monitoring change of intraocular pressure according to claim 10, further comprising:
calculating period change data according to an initial period and each current period.

* * * * *